(12) United States Patent
Hinterding et al.

(10) Patent No.: US 7,728,020 B2
(45) Date of Patent: Jun. 1, 2010

(54) AMINO ACID DERIVATIVES

(75) Inventors: Klaus Hinterding, Wittlingen (DE); Klemens Högenauer, Vienna (AT)

(73) Assignee: Novartis AG, Basel (CH)

( * ) Notice: Subject to any disclaimer, the term of this patent is extended or adjusted under 35 U.S.C. 154(b) by 780 days.

(21) Appl. No.: 10/591,774

(22) PCT Filed: Mar. 8, 2005

(86) PCT No.: PCT/EP2005/002447

§ 371 (c)(1),
(2), (4) Date: Oct. 18, 2006

(87) PCT Pub. No.: WO2005/085179

PCT Pub. Date: Sep. 15, 2005

(65) Prior Publication Data

US 2007/0135501 A1 Jun. 14, 2007

(30) Foreign Application Priority Data

Mar. 9, 2004 (GB) ................... 0405289.0

(51) Int. Cl.
*A61K 31/423* (2006.01)
*A61K 31/335* (2006.01)
*C07D 263/54* (2006.01)
*C07D 317/46* (2006.01)

(52) U.S. Cl. ................ 514/376; 548/215; 548/221; 549/429; 549/432; 549/434; 564/305; 514/461; 514/465; 514/646

(58) Field of Classification Search ............. 564/305; 562/405, 433; 514/568, 646, 376, 461, 465; 548/215, 221; 549/429, 432, 434

See application file for complete search history.

(56) References Cited

FOREIGN PATENT DOCUMENTS

WO     02/076995     10/2002
WO     03/099192     12/2003

OTHER PUBLICATIONS

Winn et al., "Homologs of dopa, .alpha.-methyldopa, and dopamine as potential cardiovascular drugs", Journal of Medicinal Chemistry, vol. 18, No. 4, pp. 434-437 (1975).

Lane et al., "A new method for the stereoselective synthesis of .alpha.-substituted serine amino acid analogues", Organic Letters, vol. 5, No. 22, pp. 4017-4020 (2003).

Kiuchi et al., "Synthesis and immunosuppressive activity of 2-substituted 2-aminopropane-1,3-diols and 2-aminoethanols", Journal of Medicinal Chemistry, vol. 43, No. 15, pp. 2946-2961 (2000).

Shtacher et al., "Iodophenyl derivatives of .alpha.-methyl alanine and isovaline as potential oral cholecystographic agents", Journal of Medicinal Chemistry, vol. 15, No. 11, pp. 1174-1177 (1972).

Harding et al., "The preparation and alkylation of a butanedione-derived chiral glycine equivalent and its use for the synthesis of alpha-amino acids and alpha,alpha-disubstituted amino acids", Tetrahedron, vol. 60, No. 35, pp. 7679-7692 (2004).

*Primary Examiner*—Golam M Shameem
(74) *Attorney, Agent, or Firm*—Hoxie & Associates LLC

(57) ABSTRACT

The present invention relates to new amino acid derivatives, process for the production, their use, in particular in transplantation, and pharmaceutical compositions containing them.

6 Claims, No Drawings

AMINO ACID DERIVATIVES

The present invention relates to amino acid derivatives, process for their production, their uses and pharmaceutical compositions containing them.

More particularly, the invention provides a compound of formula I

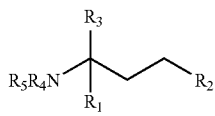
I wherein
$R_1$ is $C_{1-6}$alkyl optionally substituted by OH, $C_{1-2}$alkoxy or 1 to 6 fluorine atoms; $C_{2-6}$alkenyl; or $C_{2-6}$alkynyl;
$R_2$ is a radical of formula a, b or c

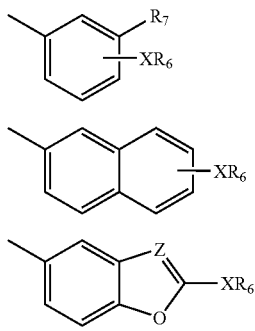

wherein
$R_6$ is $C_{1-12}$alkyl optionally substituted by halogen, by an optionally substituted cycloalkyl, by an optionally substituted phenyl, by an optionally substituted heteroaryl, or by an optionally substituted heterocyclic residue, wherein the $C_{1-12}$alkyl optionally is interrupted by one or more O or C=O; and wherein the phenyl, heteroaryl, cycloalkyl, and/or heterocyclic residue may be substituted by 1 to 5 substituents selected from hydroxy; halogen; $C_{1-4}$alkyl; $C_{1-4}$alkyl substituted by 1 to 5 fluorine atoms; $C_{1-4}$alkoxy; $C_{1-4}$alkoxy substituted by 1 to 5 fluorine atoms; cyano; phenyl; and phenyl substituted by 1 to 5 substituents selected from hydroxy, halogen, $C_{1-4}$alkyl, $C_{1-4}$alkyl substituted by 1 to 5 fluorine atoms, $C_{1-4}$alkoxy, $C_{1-4}$alkoxy substituted by 1 to 5 fluorine atoms, and cyano;
$R_7$ is H, optionally substituted phenyl, optionally substituted heteroaryl, wherein the phenyl and/or heteroaryl independently may be substituted by 1 to 5 substituents selected from hydroxy; halogen; $C_{1-4}$alkyl; $C_{1-4}$alkyl substituted by 1 to 5 fluorine atoms; $C_{1-4}$alkoxy; $C_{1-4}$alkoxy substituted by 1 to 5 fluorine atoms; and cyano;
X is O, C=O, S or a bond;
Z is N or CH;
$R_3$ is -A-B—COOH wherein each of A and B, independently is a bond, C=O or CDE, wherein each of D and E, independently is H, halogen, $C_{1-3}$alkyl, OH; with the proviso that A and B are not both C=O; and each of $R_4$ and $R_5$, independently, is H, $C_{1-4}$alkyl optionally substituted by 1, 2 or 3 halogen atoms, or acyl;
in free form or in salt form.

Alkyl or alkyl moiety may be straight or branched chain, e.g. methyl, ethyl, propyl, iso-propyl or butyl. Alkenyl may be e.g. vinyl. Alkynyl may be e.g. propyn-2-yl. Cycloalkyl may be e.g. $C_{3-6}$cycloalkyl.

Acyl may be a residue W—CO wherein W is $C_{1-6}$alkyl, $C_{3-6}$cycloalkyl, phenyl or phenyl$C_{1-4}$alkyl.

Halogen may be F, Cl or Br, preferably F or Cl.

Heteroaryl may be a 5 to 8 membered aromatic ring comprising 1 to 4 heteroatoms selected from N, O and S, e.g. pyridyl, pyrimidinyl, pyrazinyl, furyl, oxazolyl, isoxazolyl, thiophenyl, thiazolyl, isothiazolyl, pyrrolyl, imidazolyl, or pyrazolyl.

By heterocyclic residue is meant a 3 to 8, preferably 5 to 8, membered saturated or unsaturated heterocyclic ring comprising e.g. tetrahydrofuryl, tetrahydropyranyl, aziri-dinyl, piperidinyl, pyrrolidinyl, piperazinyl.

Compounds of formula I may exist in free form or in salt form, e.g. addition salts with e.g. inorganic acids, such as hydrochloride, hydrobromide or sulfate, salts with organic acids, such as acetate, fumarate, maleate, benzoate, citrate, malate, methanesulfonate or benzenesulfonate salts; the carboxylate group may also be present in salt form, e.g. an ammonium salt or salts with metals such as sodium, potassium, calcium, zinc or magnesium, or a mixture thereof. Compounds of formula I and their salts, in hydrate or solvate form are also part of the invention.

When the compounds of formula I have asymmetric centers in the molecule, various optical, isomers are obtained. The present invention also encompasses enantiomers, racernates, diastereoisomers and mixtures thereof. For example, the central carbon atom bearing $R_1$, $R_3$ and $NR_4R_5$ may have the R or S configuration. Compounds having the following 3-dimensional configuration are generally preferred:

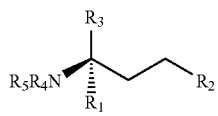

Moreover, when the compounds of formula I include geometric isomers, the present invention embraces cis-compounds, trans-compounds and mixtures thereof. Similar considerations apply in relation to starting materials exhibiting asymmetric carbon atoms or unsaturated bonds as mentioned above, e.g. compounds of formula II, III or IV as indicated below.

In the compounds of formula I, the following significances are preferred individually or in any sub-combination:

1. $R_1$ is $CH_3$ or $CH_2$—OH;

2. $R_3$ is $CH_2$—COOH;

3. each of $R_4$ and $R_5$ is hydrogen;

4. $R_7$ is hydrogen, phenyl or thiophenyl;

5. X is O or bond; and 6. if $R_2$ is a radical of formula a, $XR_6$ is para to —$(CH_2)_2$—$CR_1R_3(NR_4R_5)$.

The present invention also includes a process for the preparation of a compound of formula I which process comprises removing the protecting group present in a compound of formula II

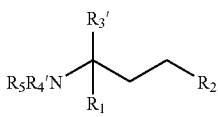

II wherein $R_1$, $R_2$ and $R_5$ are as defined above, $R'_3$ is -A-B—COOR$_8$ wherein A and B are as defined above and $R_8$ is a hydrolysable or hydrogenolysable group and $R'_4$ is an amino protecting group, and, where required, converting the compounds of formula I obtained in free form into the desired salt form, or vice versa.

Removal of the protecting group may be carried out in accordance with methods known in the art. The removal of the amino protecting groups may conveniently be performed according to methods known in the art, e.g. by hydrolysis, e.g. in an acidic medium, for example using hydrochloric acid. Examples of protecting groups for amino groups are e.g. as disclosed in "Protective Groups in Organic Synthesis" T. W. Greene, J. Wiley & Sons NY, $2^{nd}$ ed., chapter 7, 1991, and references therein, e.g. benzyl, p-methoxybenzyl, methoxymethyl, tetrahydropyranyl, trialkylsilyl, acyl, tert.-butoxycarbonyl, benzyloxycarbonyl, 9-fluorenyl methoxy carbonyl, trifluoroacetyl, and the like.

The present invention also includes a process for the preparation of a compound of formula II, wherein X is O, which process comprises alkylating a compound of formula III

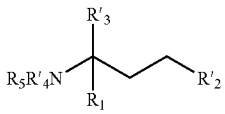

III wherein $R_1$, $R_3'$, $R_4'$ and $R_5$ are as defined above, and $R'_2$ is a radical of formula a', or b'

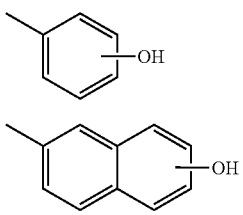

a' b' to introduce the desired residue $R_6$.

Alkylation of the compounds of formula III may be performed according to methods known in the art, e.g. by nucleophilic substitution, e.g. by reaction with an alkylating agent $R_6$—$X_3$ wherein $X_3$ is mesylate, tosylate, triflate, nosylate or an halogen, e.g. chloride, bromide or iodide. The alkylation may also be carried out by following the Mitsunobu protocol (e.g. as disclosed in Hughes, Organic Preparations and Procedures International 28, 127-64, 1996 or D. L. Hughes, Org. React. 42, 335, 1992), in solution or on solid phase support synthesis, e.g. by attaching the compound of formula III to a resin. Alternatively, either triphenylphosphine or e.g. diethyl azocarboxylate bound to a resin, e.g. polystyrene, can be used.

The present invention also includes a process for the preparation of a compound of formula I which process comprises hydrolyzing the cyano group present in a compound of formula IV

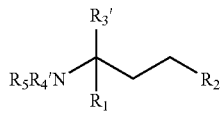

IV wherein $R_1$, $R_2$ and $R_5$ are as defined above, $R'_3$ is -A-B—CN and $R'_4$ is an amino protecting group, and, where required, converting the compounds of formula I obtained in free form into the desired salt form, or vice versa.

Insofar as the production of the starting materials is not particularly described, the compounds are known or may be prepared analogously to methods known in the art or as disclosed in the Examples hereinafter.

The following Examples are illustrative of the invention. Melting points are uncorrected.

| | |
|---|---|
| RT = | room temperature |
| DMF = | dimethylformamide |
| HPLC = | high performance liquid chromatography |
| DMSO = | dimethylsulfoxide |
| THF = | tetrahydrofuran |
| AcOEt = | ethyl acetate |

EXAMPLE 1

(R)-3-Amino-5-(4-heptyloxy-phenyl)-3-methyl-pentanoic acid

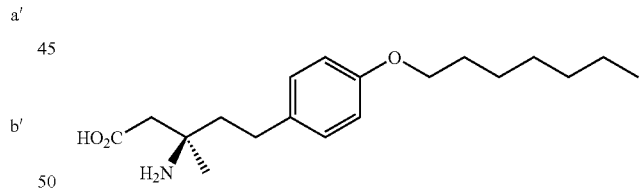

In a microwave vessel, a stirred solution of ([(R)-1-cyanomethyl-3-(4-heptyloxy-phenyl)-1-methyl-propyl]-carbamic acid tert-butyl ester (136 mg, 0.34 mMol) in dioxane (2 ml) is treated with HCl (37% aqueous solution, 1 ml). The mixture is heated to 160° C. for 1.3 hours. The reaction mixture is then cooled to RT and concentrated under reduced pressure. Preparative HPLC eluting with 5%→95% acetonitril in $H_2O$ (+0.1% trifluoro acetic acid) gives the title compound as an amorphous white powder.

$^1$H-NMR (d6-DMSO): 7.95 (brs, 1H), 7.06 (d, J=9 Hz, 2H), 6.83 (d, J=9 Hz, 2H), 3.89 (t, J=7 Hz, 2H), 3.40-3.20 (m, 2H), 2.53-2.45 (m, 2H), 1.86-1.75 (m, 2H), 1.66 (q, J=8 Hz, 2H), 1.41-1.20 (m, 11H), 0.85 (t, J=7 Hz, 3H). MS (ESI+): m/z=322.1 [M+H]$^+$

Preparation of [(R)-1-Cyanomethyl-3-(4-heptyloxy-phenyl)-1-methyl-propyl]-carbamic acid tert-butyl ester

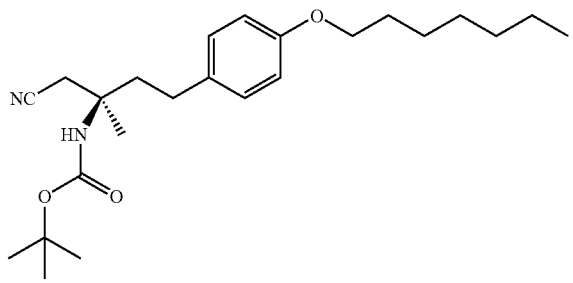

To a stirred solution of (R)-4-[2-(4-heptyloxy-phenyl)-ethyl]-4-methyl-2,2-dioxo-2λ*6*-[1,2,3]oxathiazolidine-3-carboxylic acid tert-butyl ester (174 mg, 0.40 mMol) in DMF (5 ml) is added sodium cyanide (94 mg, 1.91 mMol). The mixture is stirred at RT for 25 hours. Additional sodium cyanide (37 mg, 0.76 mMol) is added and the mixture is stirred at RT for 18 hours. The reaction mixture is then poured onto a biphasic mixture of AcOEt and NaHCO$_3$ (saturated aqueous solution). The aqueous phase is extracted twice with AcOEt. The combined organic layers are dried (Na$_2$SO$_4$) and concentrated under reduced pressure. Column chromatography eluting with 5% AcOEt in toluene gives the title compound as a colourless oil.

$^1$H-NMR (CDCl$_3$): 7.09-7.04 (m, 2H), 6.83-6.78 (m, 2H), 4.59 (br s, 1H), 3.91 (t, J=7 Hz, 2H), 3.08 (br d, J=7 Hz, 1H), 2.78 (d, J=7 Hz, 1H), 2.59-2.50 (m, 2H), 2.32-2.20 (m, 1H), 1.82-1.70 (m, 3H), 1.48 (s, 9H), 1.48-1.18 (m, 11H), 0.90 (t, J=7 Hz, 3H). MS (ESI+): m/z=468.3 [M+CH$_3$CN+Na]$^+$, 827.6 [2M+Na]$^+$.

Preparation of (R)-4-[2-(4-Heptyloxy-phenyl)-ethyl]-4-methyl-2,2-dioxo-2λ=*6*-[1,2,3]oxathiazolidine-3-carboxylic acid tert-butyl ester

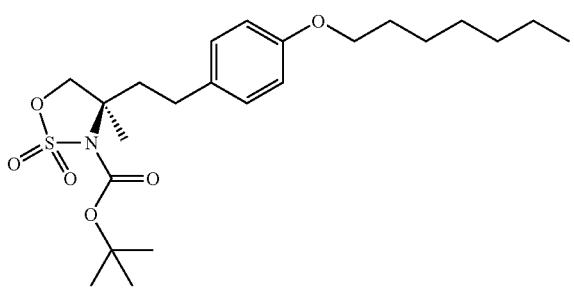

To a stirred solution of (R)-4-[2-(4-heptyloxy-phenyl)-ethyl]-4-methyl-2-oxo-[1,2,3]oxathiazolidine-3-carboxylic acid tert-butyl ester (275 mg, 0.63 mMol) in acetonitril/H$_2$O (9/1, 10 ml) is added sodium periodate (401 mg, 1.88 mMol) and ruthenium(III) chloride (13 mg, 0.06 mMol). The mixture is stirred at RT for 18 hours. Additional ruthenium(III) chloride (65 mg, 0.30 mMol) is added and the mixture is stirred at RT for 65 hours. The reaction mixture is then filtered over a pad of celite, and the filtrate is poured onto a biphasic mixture of AcOEt and Na$_2$S$_2$O$_3$ (saturated aqueous solution). The aqueous phase is extracted three times with AcOEt. The combined organic layers are dried (Na$_2$SO$_4$) and concentrated under reduced pressure. Column chromatography eluting with 5%→15% AcOEt in heptane gives the title compound a colourless oil.

$^1$H-NMR (CDCl$_3$): 7.07 (d, J=8 Hz, 2H), 6.81 (d, J=8 Hz, 2H), 4.42 (d, J=9 Hz, 1H), 4.16 (d, J=9 Hz, 1H), 3.92 (t, J=6 Hz, 2H), 2.67-2.50 (m, 2H), 2.43-2.32 (m, 1H), 2.09-1.95 (m, 1H), 1.75 (qt, J=7 Hz, 2H), 1.62 (s, 3H), 1.53 (s, 9H), 1.50-1.22 (m, 8H), 0.90 (t, J=7 Hz, 3H). MS (ESI+): m/z=478.2 [M+Na]$^+$, 933.4 [2M+Na]$^+$.

Preparation of (R)-4-[2-(4-Heptyloxy-phenyl)-ethyl]-4-methyl-2-oxo-[1,2,3]oxathiazolidine-3-carboxylic acid tert-butyl ester

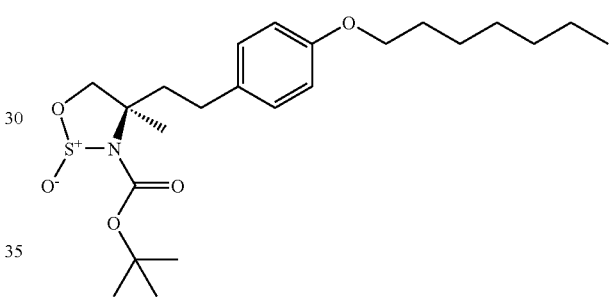

A stirred solution of thionyl chloride (0.14 ml, 1.91 mMol) in acetonitril (10 ml) is cooled to −40° C. At this temperature, a solution of [(R)-3-(4-heptyloxy-phenyl)-1-hydroxymethyl-1-methyl-propyl]-carbamic acid tert-butyl ester (300 mg, 0.76 mMol) in acetonitril (5 ml), and pyridine (0.31 ml, 3.81 mMol) are added successively. The mixture is allowed to warm to −10° C. over 2.5 hours. The reaction mixture is then poured onto a biphasic mixture of AcOEt and HCl (aqueous, 1 M). The aqueous phase is extracted twice with AcOEt. The combined organic layers are washed with NaHCO$_3$ (saturated aqueous solution), dried (Na$_2$SO$_4$) and concentrated under reduced pressure. Column chromatography eluting with 5%→15% AcOEt in heptane gives the title compounds as colourless oils (2 diastereomers, dr=1:1).

Diastereomer 1: $^1$H-NMR (CDCl$_3$): 7.07 (d, J=9 Hz, 2H), 6.81 (d, J=9 Hz, 2H), 4.95 (br d, J=9 Hz, 1H), 4.28 (d, J=9 Hz, 1H), 3.92 (t, J=6 Hz, 2H), 2.62 (dt, J=5 Hz, 8 Hz, 1H), 2.50 (dt, J=5 Hz, 8 Hz, 1H), 2.40-2.28 (m, 1H), 2.10-1.99 (m, 1H), 1.76 (qt, J=7 Hz, 2H), 1.66-1.23 (m, 20H), 0.90 (t, J=7 Hz, 3H). MS (ESI+): m/z=462.3 [M+Na]$^+$, 901.6 [2M+Na]$^+$.

Diastereomer 2: $^1$H-NMR (CDCl$_3$): 7.04 (d, J=8 Hz, 2H), 6.80 (d, J=8 Hz, 2H), 4.82 (br d, J=9 Hz, 1H), 4.59 (d, J=9 Hz, 1H), 3.91 (t, J=7 Hz, 2H), 2.59 (dt, J=8 Hz, 1H), 2.39 (dt, J=5 Hz, 7 Hz, 1H), 2.28-2.16 (m, 1H), 1.93-1.82 (m, 1H), 1.80-1.22 (m, 22H), 0.90 (t, J=7 Hz, 3H). MS (ESI+): m/z=462.3 [M+Na]$^+$, 901.6 [2M+Na]$^+$.

Preparation of [(R)-3-(4-Heptyloxy-phenyl)-1-hydroxymethyl-1-methyl-propyl]-carbamic acid tert-butyl ester

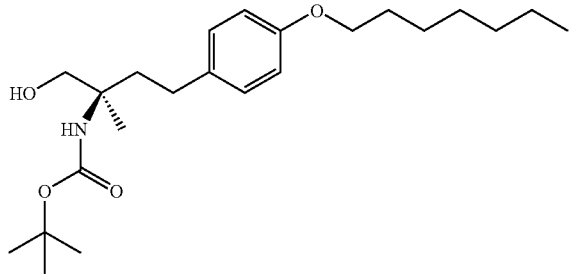

To a stirred solution of [(R)-1-hydroxymethyl-3-(4-hydroxy-phenyl)-1-methyl-propyl]-carbamic acid tert-butyl ester (2.06 g, 6.98 mMol) in ethanol (100 ml) is added potassium carbonate (2.90 g, 20.8 mMol) and methanesulfonic acid heptyl ester (2.04 g, 10.5 mMol). The mixture is heated to reflux temperature and stirred at that temperature for 6 hours. The mixture is then cooled to RT and stirred at RT overnight. The reaction mixture is then poured onto a biphasic mixture of AcOEt and HCl (aqueous, 1 M). The aqueous phase is extracted twice with AcOEt. The combined organic layers are washed with NaHCO$_3$ (saturated aqueous solution), dried (Na$_2$SO$_4$) and concentrated under reduced pressure. Column chromatography eluting with 8% AcOEt in toluene gives the title compound as a colourless oil.

$^1$H-NMR (CDCl$_3$): 7.10-7.05 (m, 2H), 6.81-6.76 (m, 2H), 4.60 (br s, 1H), 4.07 (br s, 1H), 3.92 (t, J=6 Hz, 2 H), 3.70 (d, J=12 Hz, 1H), 3.62 (d, J=12 Hz, 1H), 2.65-2.43 (m, 2H), 2.07-1.94 (m, 1H), 1.88-1.69 (m, 1H), 1.68-1.60 (m, 2H), 1.45 (s, 9H), 1.50-1.25 (m, 8H), 1.22 (s, 3H), 0.88 (t, J=7 Hz, 3H). MS (ESI+): m/z=416.1 [M+Na]$^+$.

EXAMPLE 2

(R)-2-Amino-4-(4-heptyloxy-phenyl)-2-methyl-butanoic acid

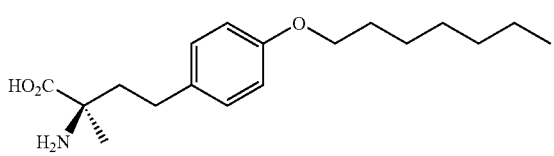

To a stirred solution of (R)-2-tert-butoxycarbonylamino-4-(4-heptyloxy-phenyl)-2-methyl-butyric acid (43 mg, 0.11 mMol) in CH$_2$Cl$_2$ (2 ml) is added trifluoroacetic acid (0.1 ml). The mixture is stirred at RT for 8 hours. After that time, the reaction mixture is concentrated under reduced pressure. Column chromatography eluting with 5%→25% MeOH in CH$_2$Cl$_2$ gives the title compound as a colourless oil.

$^1$H-NMR (d6-DMSO): 8.32 (br s, 3H), 7.02 (d, J=8 Hz, 2H), 6.81 (d, J=8 Hz, 2H), 3.88 (t, J=7 Hz, 2H), 2.70-2.58 (m, 1H), 2.42-2.31 (m, 1H), 2.04-1.83 (m, 2H), 1.70-1.62 (m, 2H), 1.45 (s, 3H), 1.44-1.21 (m, 8H), 0.72 (t, J=7 Hz, 3H). MS (ESI-): m/z=306.3 [M+H]$^+$.

Preparation of (R)-2-tert-Butoxycarbonylamino-4-(4-heptyloxy-phenyl)-2-methyl-butyric acid

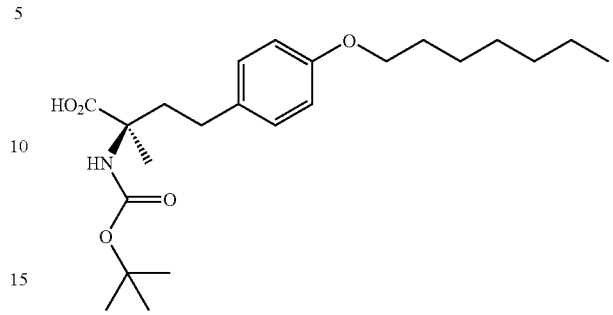

To a stirred solution of [(R)-1-formyl-3-(4-heptyloxy-phenyl)-1-methyl-propyl]-carbamic acid tert-butyl ester (103 mg, 0.26 mMol) in tert-butanol (1 ml) and 10% aqueous KH$_2$PO$_4$ (1 ml) is added 2-methyl-2-butene (0.66 ml, 5.27 mMol) and sodium chlorite (59 mg, 0.52 mMol). The mixture is stirred at RT for 1 hour. The reaction mixture is then poured onto a biphasic mixture of AcOEt and HCl (aqueous, 1M). The aqueous phase is extracted twice with AcOEt. The combined organic layers are washed with a small amount of NaHCO$_3$ (saturated aqueous solution), dried (Na$_2$SO$_4$) and concentrated under reduced pressure. Column chromatography eluting with 5% MeOH in CH$_2$Cl$_2$ gives the title compound as a colourless oil.

MS (ESI+): m/z=430.2 [M+Na]$^+$.

Preparation of [(R)-1-Formyl-3-(4-heptyloxy-phenyl)-1-methyl-propyl]-carbamic acid tert-butyl ester

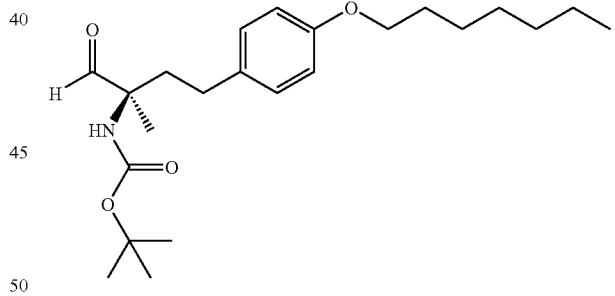

To a stirred solution of [(R)-1-hydroxymethyl-3-(4-hydroxy-phenyl)-1-methyl-propyl]-carbamic acid tert-butyl ester (1.98 g, 5.03 mMol) in CH$_2$Cl$_2$ (20 ml) is added N-morpholine-N-oxide (884 mg, 7.54 mMol) and tetra-n-propylammonium perruthenate (177 mg, 0.50 mMol). The mixture is stirred at RT for 1 hour. The mixture is then filtered over a short pad of SiO$_2$ eluting with diethyl ether. The filtrate is concentrated under reduced pressure to give the title compound. The crude product is sufficiently pure to be used in the next stage without further purification.

$^1$H-NMR (CDCl$_3$): 9.33 (s, 1H), 7.06-7.01 (m, 2H), 6.82-6.76 (m, 2H), 5.18 (brs, 1H), 3.92 (t, 2H), 2.60-2.49 (m, 1H), 2.44-2.19 (m, 2H), 2.01-1.93 (m, 1H), 1.80-1.71 (m, 2H), 1.55 (s, 3H), 1.48-1.25 (m, 17H), 0.89 (t, J=7 Hz, 3H). MS (ESI+): m/z=414.2 [M+Na]$^+$.

EXAMPLE 3

(R)-4-Amino-6-(4-heptyloxy-phenyl)-4-methyl-hexanoic acid

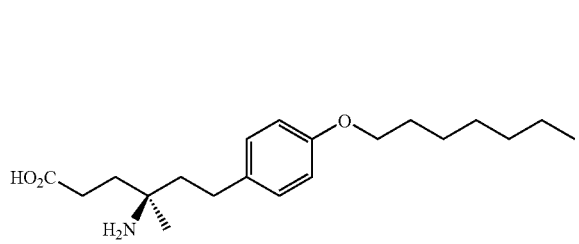

To a stirred solution of (R)-4-tert-butoxycarbonylamino-6-(4-heptyloxy-phenyl)-4-methyl-hexanoic acid (24 mg, 0.06 mMol) in $CH_2Cl_2$ (2 ml) is added trifluoroacetic acid (0.1 ml). The mixture is stirred at RT for 6.5 hours. After that time, the reaction mixture is concentrated under reduced pressure to give the title compound as an amorphous white powder. The crude product is sufficiently pure to be used without further purification.

$^1$H-NMR (d6-DMSO): 7.81 (br s, 3H), 7.12-7.07 (m, 2H), 6.85-6.81 (m, 2H), 3.90 (t, J=7 Hz, 2H), 2.52-2.29 (m, 4H), 1.88-1.80 (m, 2H), 1.77-1.62 (m, 4H), 1.40-1.21 (m, 11H), 0.85 (t, J=7 Hz, 3H). MS (ESI+): m/z=336.2 [M+H]$^+$.

Preparation of (R)-4-tert-Butoxycarbonylamino-6-(4-heptyloxy-phenyl)-4-methyl-hexanoic acid

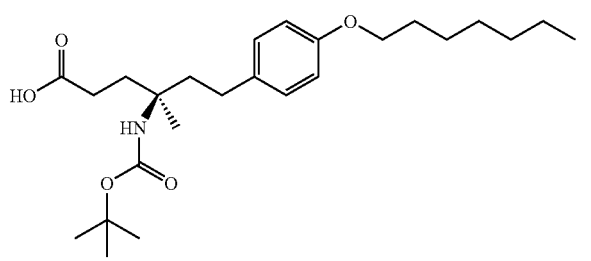

To a stirred solution of (E)-(R)-4-tert-butoxycarbonylamino-6-(4-heptyloxy-phenyl)-4-methyl-hex-2-enoic acid (53 mg, 0.12 mMol) in AcOEt (10 ml) is added palladium on charcoal (10 mg, 10%). The reaction is stirred under a $H_2$-atmosphere at RT for 17 hours. The reaction mixture is filtered over Celite and the filtrate is concentrated under reduced pressure to give the title compound as a colourless oil. The crude product is sufficiently pure to be used in the next stage without further purification.

$^1$H-NMR (CDCl$_3$): 7.06 (d, J=9 Hz, 2H), 6.80 (d, J=9 Hz, 2H), 4.42 (br s, 1H), 3.92 (t, J=6 Hz, 2H), 2.51 (t, J=8 Hz, 2H), 2.38 (t, J=8 Hz, 2H), 2.28-2.17 (m, 1H), 2.11-2.00 (m, 1H), 1.97-1.70 (m, 4H), 1.50-1.22 (m, 20H), 0.90 (t, J=7 Hz, 3H). MS (ESI-): m/z=434.4 [M-H]$^+$.

Preparation of (E)-(R)-4-tert-Butoxycarbonylamino-6-(4-heptyloxy-phenyl)-4-methyl-hex-2-enoic acid

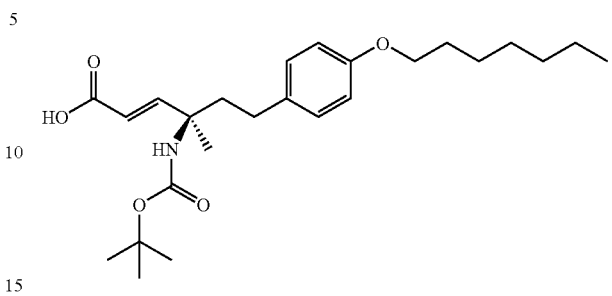

To a stirred solution of (E)-(R)-4-tert-butoxycarbonylamino-6-(4-heptyloxy-phenyl)-4-methyl-hex-2-enoic acid ethyl ester (56 mg, 0.12 mMol) in methanol (0.5 ml), THF (0.5 ml) and water (0.5 ml) is added lithium hydroxide (14 mg, 0.61 mMol). The mixture is stirred at RT for 3.5 hours. The reaction mixture is then poured onto a biphasic mixture of AcOEt and HCl (aqueous, 1 M). The aqueous phase is extracted twice with AcOEt. The combined organic layers are washed with a small amount of NaHCO$_3$ (saturated aqueous solution), dried (Na$_2$SO$_4$) and concentrated under reduced pressure to give the title compound. The crude product is sufficiently pure to be used in the next stage without further purification.

$^1$H-NMR (d6-DMSO): 12.3 (br s, 1H), 7.08-7.00 (m, 2H), 6.91 (br s, 1H), 6.83 (d, J=16 Hz, 1H), 6.79-6.75 (m, 2H), 5.67 (d, J=16 Hz, 1H), 3.88 (t, J=7 Hz, 2H), 2.50-2.31 (m, 1H), 2.00-1.89 (m, 1H), 1.79-1.60 (m, 4H), 1.40-1.19 (m, 20H), 0.83 (t, J=7 Hz, 3H), MS (ESI+): m/z=456.3 [M+Na]$^+$.

Preparation of (E)-(R)-4-tert-butoxycarbonylamino-6-(4-heptyloxy-phenyl)-4-methyl-hex-2-enoic acid ethyl ester

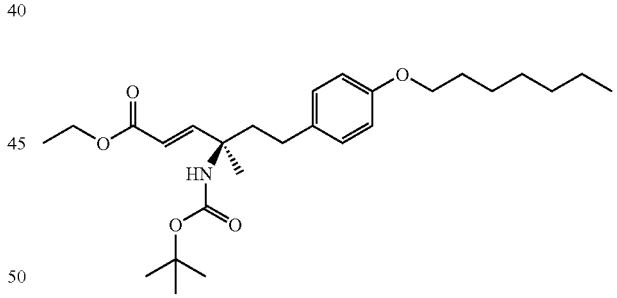

To a stirred solution of (diethoxy-phosphoryl)-acetic acid ethyl ester (429 mg, 1.92 mMol) in dry THF (7 ml) is added n-butyllithium (0.66 ml, 2.5M in hexane, 1.66 mMol) at −78° C. The mixture was stirred at −78° C. for 1 hour. After that time, a solution of [(R)-1-formyl-3-(4-heptyloxy-phenyl)-1-methyl-propyl]-carbamic acid tert-butyl ester (500 mg, 1.28 mMol) in THF (4 ml) is added and stirring is continued at −78° C. for 1.5 hours. The mixture is allowed to warm to RT and then stirred at RT for 2 hours. The reaction mixture is then poured onto a biphasic mixture of AcOEt and NaHCO$_3$ (saturated aqueous solution) and the aqueous phase is extracted twice with AcOEt. The combined organic layers are dried (Na$_2$SO$_4$) and concentrated under reduced pressure. Column chromatography eluting with 4% AcOEt in toluene gives the title compound as a colourless oil.

$^1$H-NMR (CDCl$_3$): 7.10-7.01 (m, 2H), 7.00 (d, J=16 Hz, 1H), 6.83-6.78 (m, 2H), 5.86 (d, J=16 Hz, 1H), 4.60 (br s, 1H), 4.20 (q, J=7 Hz, 2H), 3.92 (t, J=7 Hz, 2H), 2.55-2.48 (m, 2H), 2.11-2.01 (m, 1H), 1.99-1.86 (m, 1H), 1.80-1.71 (m, 2H), 1.56 (s, 3H), 1.48-1.22 (m, 20 H), 0.89 (t, J=7 Hz, 3H).

The compounds of formula I in free form or in pharmaceutically acceptable salt form, exhibit valuable pharmacological properties, e.g. lymphocyte recirculation modulating properties, e.g. as indicated in in vitro and in vivo tests and are therefore indicated for therapy.

A. In vitro

The compounds of formula I have binding affinity to individual human S1P receptors as determined in following assays:

Sphingosine-1-phosphate (SIP) Receptor Profiling

Agonist activities of compounds are tested on the human S1P receptors EDG-1 (S1P$_1$), EDG-3 (S1P$_3$), EDG-5 (S1P$_2$), EDG-6 (S1P$_4$) and EDG-8 (S1P$_5$). Functional receptor activation is assessed by quantifying compound induced GTP [$\gamma$-$^{35}$S] binding to membrane protein prepared from transfected CHO or RH7777 cells stably expressing the appropriate human S1P receptor. The assay technology used is SPA (scintillation proximity based assay). Briefly, DMSO dissolved compounds are serially diluted and added to SPA-based (Amersham-Pharmacia) immobilised S1P receptor expressing membrane protein (10-20 μg/well) in the presence of 50 mM Hepes, 100 mM NaCl, 10 mM MgCl$_2$, 10 μM GDP, 0.1% fat free BSA and 0.2 nM GTP [$\gamma^{35}$S] (1200 Ci/mmol). After incubation in 96 well microtiterplates at RT for 120 min, unbound GTP [$\gamma^{35}$S] is separated by a centrifugation step. Luminescence of SPA beads triggered by membrane bound GTP [$\gamma^{35}$S] is quantified with a TOPcount plate reader (Packard). EC$_{50}$s are calculated using standard curve fitting software. In this assay, the compounds of formula I have a binding affinity to S1P$_1$ receptor <50 nM.

| Example | S1P$_1$ EC$_{50}$ [nM] | S1P$_3$ EC$_{50}$ [nM] | S1P$_4$ EC$_{50}$ [nM] | S1P$_5$ EC$_{50}$ [nM] |
|---|---|---|---|---|
| 1 | 11 Agon | 209 Agon | 117 Agon | 203 Agon |

Agon = agonist

B. In vivo: Blood Lymphocyte Depletion

A compound of formula I or the vehicle is administered orally by gavage to rats. Tail blood for hematological monitoring is obtained on day −1 to give the baseline individual values, and at 2, 6, 24, 48 and 72 hours after application. In this assay, the compounds of formula I deplete peripheral blood lymphocytes when administered at a dose of 0.03 to 3 mg/kg. For example, following results are obtained: depletion of peripheral blood lymphocytes by more than 50%.

EXAMPLE 1

3.2 mg/kg p.o. after 6 h

The compounds of formula I are, therefore, useful in the treatment and/or prevention of diseases or disorders mediated by lymphocytes interactions, e.g. in transplantation, such as acute or chronic rejection of cell, tissue or organ allo- or xenografts or delayed graft function, graft versus host disease, autoimmune diseases, e.g. rheumatoid arthritis, systemic lupus erythematosus, hashimoto's thyroidis, multiple sclerosis, myasthenia gravis, diabetes type I or II and the disorders associated therewith, vasculitis, pernicious anemia, Sjoegren syndrome, uveitis, psoriasis, Graves ophthalmopathy, alopecia areata and others, allergic diseases, e.g. allergic asthma, atopic dermatitis, allergic rhinitis/conjunctivitis, allergic contact dermatitis, inflammatory diseases optionally with underlying aberrant reactions, e.g. inflammatory bowel disease, Crohn's disease or ulcerative colitis, intrinsic asthma, inflammatory lung injury, inflammatory liver injury, inflammatory glomerular injury, atherosclerosis, osteoarthritis, irritant contact dermatitis and further eczematous dermatitises, seborrhoeic dermatitis, cutaneous manifestations of immunologically-mediated disorders, inflammatory eye disease, keratoconjunctivitis, myocarditis or hepatitis, ischemia/reperfusion injury, e.g. myocardial infarction, stroke, gut ischemia, renal failure or hemorrhage shock, traumatic shock, angiogenesis, Alzheimer's disease, cancer, e.g. breast cancer, T cell lymphomas or T cell leukemias, infectious diseases, e.g. toxic shock (e.g. superantigen induced), septic shock, adult respiratory distress syndrome or viral infections, e.g. AIDS, viral hepatitis, chronic bacterial infection, or senile dementia. Examples of cell, tissue or solid organ transplants include e.g. pancreatic islets, stem cells, bone marrow, corneal tissue, neuronal tissue, heart, lung, combined heart-lung, kidney, liver, bowel, pancreas, trachea or oesophagus. For the above uses the required dosage will of course vary depending on the mode of administration, the particular condition to be treated and the effect desired.

In general, satisfactory results are indicated to be obtained systemically at daily dosages of from about 0.03 to 2.5 mg/kg per body weight. An indicated daily dosage in the larger mammal, e.g. humans, is in the range from about 0.5 mg to about 100 mg, conveniently administered, for example, in divided doses up to four times a day or in retard form. Suitable unit dosage forms for oral administration comprise from ca. 0.1 to 50 mg active ingredient.

The compounds of formula I may be administered by any conventional route, in particular enterally, e.g. orally, e.g. in the form of tablets or capsules, or parenterally, e.g. in the form of injectable solutions or suspensions, topically, e.g. in the form of lotions, gels, ointments or creams, or in a nasal or a suppository form. Pharmaceutical compositions comprising a compound of formula I in free form or in pharmaceutically acceptable salt form in association with at least one pharmaceutical acceptable carrier or diluent may be manufactured in conventional manner by mixing with a pharmaceutically acceptable carrier or diluent.

The compounds of formula I may be administered in free form or in pharmaceutically acceptable salt form e.g. as indicated above. Such salts may be prepared in conventional manner and exhibit the same order of activity as the free compounds.

In accordance with the foregoing the present invention further provides:

1.1 A method for preventing or treating disorders or diseases mediated by lymphocytes, e.g. such as indicated above, in a subject in need of such treatment, which method comprises administering to said subject an effective amount of a compound of formula I or a pharmaceutically acceptable salt thereof;

1.2 A method for preventing or treating acute or chronic transplant rejection or T-cell mediated inflammatory or autoimmune diseases, e.g. as indicated above, in a subject in need of such treatment, which method comprises administering to said subject an effective amount of a compound of formula I or a pharmaceutically acceptable salt thereof;

2. A compound of formula I, in free form or in a pharmaceutically acceptable salt form for use as a pharmaceutical, e.g. in any of the methods as indicated under 1.1 or 1.2 above.

3. A pharmaceutical composition, e.g. for use in any of the methods as in 1.1 or 1.2 above comprising a compound of formula I in free form or pharmaceutically acceptable salt form in association with a pharmaceutically acceptable diluent or carrier therefor.

4. A compound of formula I or a pharmaceutically acceptable salt thereof for use in the preparation of a pharmaceutical composition for use in any of the method as in 1.1 or 1.2 above.

The compounds of formula I may be administered as the sole active ingredient or in conjunction with, e.g. as an adjuvant to, other drugs e.g. immunosuppressive or immunomodulating agents or other anti-inflammatory agents, e.g. for the treatment or prevention of allo- or xenograft acute or chronic rejection or inflammatory or autoimmune disorders, or a chemotherapeutic agent, e.g a malignant cell anti-proliferative agent. For example, the compounds of formula I may be used in combination with a calcineurin inhibitor, e.g. cyclosporin A, FK 506 or ISA$_{TX}$247; a mTOR inhibitor, e.g. rapamycin, 40-O-(2-hydroxyethyl)-rapamycin, CCI779, ABT578, AP23573, AP23464, AP23675, AP23841, TAFA-93, biolimus 7 or biolimus 9; an ascomycin having immunosuppressive properties, e.g. ABT-281, ASM981, etc.; corticosteroids; cyclophosphamide; azathioprene; methotrexate; leflunomide; mizoribine; mycophenolic acid; mycophenolate mofetil; 15-deoxyspergualine or an immunosuppressive homologue, analogue or derivative thereof; immunosuppressive monoclonal antibodies, e.g. monoclonal antibodies to leukocyte receptors, e.g., MHC, CD2, CD3, CD4, CD7, CD8, CD25, CD28, CD40. CD45, CD58, CD80, CD86 or their ligands; other immunomodulatory compounds, e.g. a recombinant binding molecule having at least a portion of the extracellular domain of CTLA4 or a mutant thereof, e.g. an at least extracellular portion of CTLA4 or a mutant thereof joined to a non-CTLA4 protein sequence, e.g. CTLA4Ig (for ex. designated ATCC 68629) or a mutant thereof, e.g. LEA29Y; adhesion molecule inhibitors, e.g. LFA-1 antagonists, ICAM-1 or -3 antagonists, VCAM-4 antagonists or VLA-4 antagonists; or a chemotherapeutic agent, e.g. paclitaxel, gemcitabine, cisplatinum, doxorubicin or 5-fluorouracil; or an anti-infective agent.

Where the compounds of formula I are administered in conjunction with other immuno-suppressive/immunomodulatory, anti-inflammatory, chemotherapeutic or anti-infectious therapy, dosages of the co-administered immunosuppressant, immunomodulatory, anti-inflammatory, chemotherapeutic or anti-infectious compound will of course vary depending on the type of co-drug employed, e.g. whether it is a steroid or a calcineurin inhibitor, on the specific drug employed, on the condition being treated and so forth. In accordance with the foregoing the present invention provides in a yet further aspect:

5. A method as defined above comprising co-administration, e.g. concomitantly or in sequence, of a therapeutically effective non-toxic amount of a compound of formula I and at least a second drug substance, e.g. an immunosuppressant, immuno-modulatory, anti-inflammatory or chemotherapeutic drug, e.g. as indicated above.

6. A pharmaceutical combination, e.g. a kit, comprising a) a first agent which is a compound of formula I as disclosed herein, in free form or in pharmaceutically acceptable salt form, and b) at least one co-agent, e.g. an immunosuppressant, immunomodulatory, anti-inflammatory, chemotherapeutic or anti-infectious agent. The kit may comprise instructions for its administration.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

The term "pharmaceutical combination" as used herein means a product that results from the mixing or combining of more than one active ingredient and includes both fixed and non-fixed combinations of the active ingredients. The term "fixed combination" means that the active ingredients, e.g. a compound of formula I and a co-agent, are both administered to a patient simultaneously in the form of a single entity or dosage. The term "non-fixed combination" means that the active ingredients, e.g. a compound of formula I and a co-agent, are both administered to a patient as separate entities either simultaneously, concurrently or sequentially with no specific time limits, wherein such administration provides therapeutically effective levels of the 2 compounds in the body of the patient. The latter also applies to cocktail therapy, e.g. the administration of 3 or more active ingredients.

The invention claimed is:

1. A compound of formula I

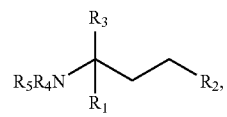

I wherein
R$_1$ is C$_{1-6}$-alkyl optionally substituted by OH, C$_{1-2}$-alkoxy or 1-to-6 fluorine atoms; C$_{2-6}$-alkenyl; or C$_{2-6}$-alkynyl;
R$_2$ is a radical of formula a or b

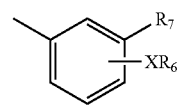

a

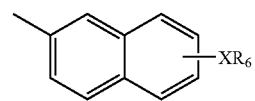

b where
R$_6$ is C$_{1-12}$-alkyl optionally substituted by halogen, by an optionally-substituted cycloalkyl, by an optionally-substituted phenyl, by an optionally-substituted heteroaryl, or by an optionally-substituted heterocyclic residue, wherein the C$_{1-12}$-alkyl optionally is interrupted by one or more O or C=O; and wherein the phenyl, heteroaryl, cycloalkyl, and/or heterocyclic residue may be substituted by 1-to-5 substituents independently selected from hydroxy; halogen; C$_{1-4}$-alkyl; C$_{1-4}$-alkyl substituted by 1-to-5 fluorine atoms; C$_{1-4}$-alkoxy; C$_{1-4}$-alkoxy substituted by 1-to-5 fluorine atoms; cyano; phenyl; and phenyl substituted by 1-to-5 substituents independently selected from hydroxy, halogen, C$_{1-4}$-alkyl, C$_{1-4}$-alkoxy, and cyano;
R$_7$ is H, optionally-substituted phenyl, optionally-substituted heteroaryl, wherein the phenyl and/or heteroaryl, independently, may be substituted by 1-to-5 substituents independently selected from hydroxy; halogen; $C_{1-4}$-alkyl; $C_{1-4}$-alkyl substituted by 1-to-5 fluorine atoms; $C_{1-4}$-alkoxy; $C_{1-4}$-alkoxy substituted by 1-to-5 fluorine atoms; and cyano; and X is O;

$R_3$ is -A-B—COOH, where each of A and B, independently, is a bond, C=O or CDE, wherein each of D and E, independently, is H, halogen, $C_{1-3}$-alkyl or OH; with the proviso that A and B are not both C=O; and each of $R_4$ and $R_5$, independently, is H, $C_{1-4}$-alkyl optionally substituted by 1, 2 or 3 halogen atoms, or acyl, where acyl is a residue W—CO, wherein W is $C_{1-6}$-alkyl, $C_{3-4}$-cycloalkyl, phenyl or phenyl$C_{1-4}$-alkyl;

with the proviso that when $R_4$ is H, $R_5$ is H, $R_3$ is COOH, $R_2$ is a radical of formula a and $R_7$ is H, and either i) $R_1$ is $CH_2OH$ and $XR_6$ is an unsubstituted $C_{1-12}$-alkyl that is not para to $(CH_2)_2$—$CR_1R_3(NR_4R_5)$; or ii) $R_1$ is $CH_3$ and $XR_6$ is an unsubstituted $OC_{1-12}$-alkyl that is not meta to $(CH_2)_2$—$CR_1R_3(NR_4R_5)$;

where heteroaryl is pyridyl, pyrimidinyl, pyrazinyl, furyl, oxazolyl, isoxazolyl, thiophenyl, thialzolyl, isothiazolyl, pyrrolyl, imidazolyl or pyrazolyl; cycloalkyl is $C_{3-6}$-cycloalkyl; and a heterocyclic residue is tetrahydrofuryl, tetrahydropyranyl, aziridinyl, piperidinyl, pyrrolidinyl or piperazinyl;

in free form or in salt form.

2. A compound of formula II

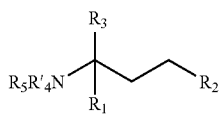

I wherein $R_1$, $R_2$, $R_3$ and $R_5$ are as defined in claim 1, and $R'_4$ is a protecting group selected from benzyl, p-methoxybenzyl, methoxymethyl, tetrahydropyranyl, trialkylsilyl, acyl, where acyl is a residue W—CO, wherein W is $C_{1-6}$-alkyl, $C_{3-6}$-cycloalkyl, phenyl or phenyl$C_{1-4}$-alkyl, tert-butoxycarbonyl, benzyloxycarbonyl, 9-fluorenylmethoxycarbonyl and trifluoroacetyl, or a salt thereof.

3. A compound according to claim 1 which is selected from (R)-3-amino-5-(4-heptyloxy-phenyl)-3-methyl-pentanoic, (R)-4-amino-6-(4-heptyloxy-phenyl)-4-methyl-hexanoic acid and (R)-2-amino-4-(4-heptyloxy-phenyl)-2-methyl-butanoic acid.

4. A pharmaceutical composition comprising a compound according to claim 1 in free form or in a pharmaceutically-acceptable salt form, together with one or more pharmaceutically-acceptable diluents or carriers therefor.

5. The pharmaceutical composition of claim 4, wherein the compound is of formula II

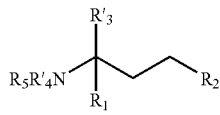

II where $R_1$, $R_2$, $R_3$ and $R_5$ are as defined in claim 1, and $R'_4$ is a protecting group, or a salt thereof.

6. The pharmaceutical composition of claim 4, wherein the compound is selected from (R)-3-amino-5-(4-heptyloxy-phenyl)-3-methyl-pentanoic acid, (R)-4-amino-6-(4-heptyloxy-phenyl)-4-methyl-hexanoic acid and (R)-2-amino-4-(4-heptyloxy-phenyl)-2-methyl-butanoic acid.

* * * * *